(12) United States Patent
Hölzl et al.

(10) Patent No.: US 6,376,522 B1
(45) Date of Patent: Apr. 23, 2002

(54) 4-HYDROXYISOTHIAZOLE COMPOUNDS

(75) Inventors: Werner Hölzl, Eschentzwiller (FR); Wolfgang Haap, Grenzach-Wyhlen (DE); Dietmar Ochs, Schopfheim (DE); Karin Puchtler, Fischingen (DE); Marcel Schnyder, Birsfelden (CH); Dinesh Narenda Rele, Mumbai (IN); Sitaram Pal, West Bengal (IN); Asawari Bhikaji Mahtre; Surendra Umesh Kulkarni, both of Mumbai (IN); Arakali Srinivasarao Radhakrishna, Bangalore (IN)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/573,781

(22) Filed: May 18, 2000

(30) Foreign Application Priority Data

May 20, 1999 (EP) .............................. 99810441

(51) Int. Cl.⁷ ................................................ A01N 43/80
(52) U.S. Cl. ....................................... 514/372; 548/209
(58) Field of Search ........................... 548/209; 514/372

(56) References Cited

U.S. PATENT DOCUMENTS 3,887,352 A      6/1975   Lewis et al. .................... 71/67

OTHER PUBLICATIONS

Chemical Abstract, vol. 69, No. 52061q, 1968 (abstract of Bull. Chem. Soc. Jap., Naito et al.)

T. Naito et al., Bulletin of the Chemical Society of Japan, vol. 41, pp. 959–964, (1968).

*Primary Examiner*—Robert Gerstl
(74) *Attorney, Agent, or Firm*—Kevin T. Mansfield

(57) ABSTRACT

The present invention relates to the use of 4-hydroxyisothiazole compounds as antimicrobially active substances, certain new 4-hydroxyisothiazole compounds and a process for their preparation.

15 Claims, No Drawings

4-HYDROXYISOTHIAZOLE COMPOUNDS

The present invention relates to the use of 4-hydroxyisothiazole compounds as antimicrobially active substances, certain new 4-hydroxyisothiazole compounds and a process for their preparation.

It is known that certain halogenated 3-hydroxyisothiazole compounds have an excellent antimicrobial activity, as disclosed in U.S. Pat. No. 3,887,352. However it is desirable to be able to provide non-halogenated agents which are highly effective antimicrobial agents. Polymeric materials can be antimicrobially finished by incorporating halogenated compounds, the active substances being, as a result of their excellent migration properties, constantly conveyed to the surface of the corresponding material ("slow release"). For certain industrial applications, this effect is undesired since the long-term effect of antimicrobially finished materials such as textiles, paper, plastics, cellulose sponges etc. is reduced at the same time.

The object of the present invention is thus to provide non-halogenated 4-hydroxyisothiazole compounds for use as antimicrobially active substances and which, at the same time, are stable to migration.

The present invention provides the use of 4-hydroxyisothiazole compounds of the following formulae

[Structures (1) and (2) shown], wherein $R_1$ and $R_2$ are independently of each other hydrogen; $C_1$–$C_{10}$ alkyl; substituted $C_1$–$C_{10}$alkyl; $C_1$–$C_{10}$acyl; substituted $C_1$–$C_{10}$acyl; $C_6$–$C_{10}$aryl; substituted $C_6$–$C_{10}$aryl; $C_6$–$C_{10}$aryl carbonyl; or substituted $C_6$–$C_{10}$arylcarbonyl; as antimicrobial agents.

Of particular interest are compounds of formula (1) as an antimicrobial wherein $R_1$ and $R_2$ are both $C_6$–$C_{10}$aryl.

A preferred compound is of formula (1) wherein $R_1$ and $R_2$ are both phenyl.

A preferred compound is of formula (2) wherein $R_2$ is $C_6$–$C_{10}$aryl or substituted $C_6$–$C_{10}$aryl.

Another aspect of the invention are certain compounds described by formula (1) and (2) which are novel. These novel compounds include compounds of formula

[Structures (1) and (2) shown], wherein $R_1$ and $R_2$ are independently of each other hydrogen; $C_1$–$C_{10}$alkyl; substituted $C_1$–$C_{10}$alkyl; $C_1$–$C_1$acyl; substituted $C_1$–$C_{10}$acyl; $C_6$–$C_{10}$aryl; substituted $C_6$–$C_{10}$aryl; $C_6$–$C_{10}$aryl carbonyl; or substituted $C_6$–$C_{10}$aryl carbonyl.

$C_1$–$C_{10}$ alkyl may be branched or unbranched such as methyl, ethyl, n-propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, n-nonyl, n-decyl.

$C_6$–$C_{10}$ aryl may be phenyl or naphtyl.

The substituted $C_1$–$C_{10}$ alkyl, substituted $C_6$–$C_{10}$ aryl and substituted $C_6$–$C_{10}$ arylcarbonyl may be substituted by halogen, preferably fluoro, $C_1$–$C_{10}$ alkoxy or $C_1$–$C_6$ alkyl carbonyl.

$C_1$–$C_{10}$ alkoxy is straight-chain or branched alkoxy radicals such as methoxy, ethoxy, n-propoxy, isopropoxy, n-butoxy, sec-butoxy, tert-butoxy, pentyloxy, isopentyloxy, tertpentyloxy, heptyloxy, octyloxy, isooctyloxy, nonyloxy or decyloxy.

$C_1$–$C_6$ alkyl carbonyl is straight-chain or branched carbonyl radicals such as acetyl, propionyl, butyryl, isobutyryl, valeryl, isovaleryl or pivaloyl.

Another aspect of the present invention is a process for the preparation of compounds of formula (1). The process comprises reacting acetic anhydride with an acetic acid substituted on the alpha carbon by $R_1$ or $R_2$, at a temperature of 120° C. to 180° C., preferably at a temperature of 140° C. to 160° C. The reaction scheme below shows the reaction, wherein $R_4$ represents $R_1$ or $R_2$ as previously defined.

[Reaction scheme shown]

The resulting ketone is then stirred with hydroxylamine hydrochloride to produce an oxime:

[Reaction scheme shown]

The oxime is then stirred with tosyl chloride in an aromatic solvent, such as pyridine, at a temperature of −5° C. to 5° C., preferably at a temperature of −2° C. to 2° C.

[Reaction scheme shown]

The tosylate is then dissolved in an ether solvent, such as tetrahydrofuran, and added to a cooled solution of potassium metal in dry alcohol, such as ethanol:

[Reaction scheme shown]

The aminoketone is then heated with thionyl chloride at a temperature of 40° C. to 60° C., preferably at a temperature of 45° C. to 55° C.:

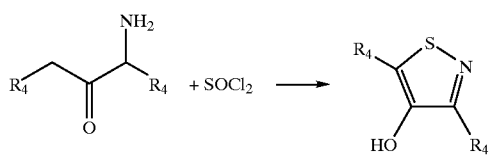

Preferably R₄ is phenyl.

Alternatively, by the reaction steps I–IV as shown in the reaction scheme below natural amino acids are obtainable which can be reacted to amino ketones in a Dakin-West reaction (step V). Compounds of formula (2) are formed as by-products:

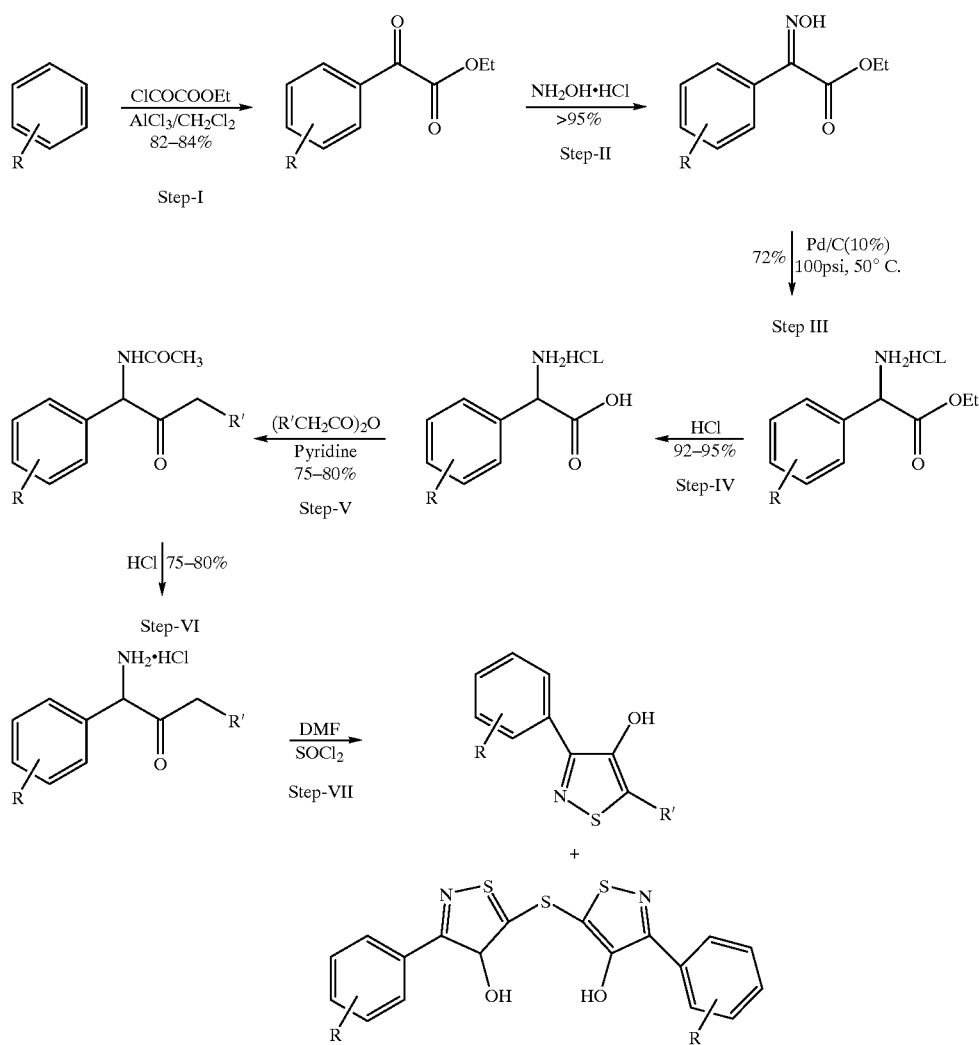

(for R' = H)
R = $C_1$–$C_{10}$alkyl; $C_1$–$C_{10}$alkoxy; halogen

The experimental procedure for step I to step IV is elaborated for substrates with R=p-Fluoro substituted compounds and a general procedure is given for the remaining steps (Step V to Step VII).

Step-I:

aluminium chloride 80 g (0.6 mol) is added To a solution of ethyl oxalyl chloride 82 g (0.6 mol) in 200 ml of dichloromethane with stirring at temperature 25–30° C. over a period of 30 minutes in portions. Fluorobenzene 48 g (0.5 mol) in 200 ml of dichloromethane is added through a dropping funnel over a period of 2.5 h, maintaining the temperature at 25–30° C. Stirring is continued at the same temperature for additional 3 h. Reaction mass is then quenched over 1 l ice-cold water containing 200 ml of $HCl_{conc}$. The organic layer is separated, passed over celite bed and dried over anhydrous $Na_2SO_4$. Dichloromethane is distilled off under reduced pressure to get 83 g (84%) of the ketone.

Step-II:

Hydroxylamine hydrochloride (12.25 g, 0.1 76 mol) is added under stirring at room temperature to a solution of the ketone (30 g, 0.153 mol) in 150 ml ethanol. Pyridine (14 ml, 0.18 mol) is added to the stirred reaction mixture and is refluxed for 2.5 h. Pyridine and ethanol are distilled off under reduced pressure. The residue is dissolved in 250 ml of ether and washed with water (200 ml). Ether extract is dried over anhydrous $Na_2SO_4$ and concentrated under reduced pressure to obtain the 32 g (99%) of oxime as a mixture of syn and anti isomers.

Step-III:

2 g of 10 % Pd-C is added to a solution of oxime (20 g, 0.095 mol) in ethanol (300 ml) and acetic acid (25 ml), taken in a 1 l autoclave. Hydrogen is charged into the autoclave till a pressure of 100 psi. The mixture is stirred at 50° C. for 5 h. The catalyst is filtered off and the filtrate is concentrated to get brown coloured sticky solid. This residue is taken in dry ether and dry HCl gas passed through it to get white crystalline amine hydrochloride (15.86 g, 72%). 3.2 g (16%) of the staring material is also recovered from ether layer.

Step-IV:

13 g (0.055mol) of the α-amino ester hydrochloride is hydrolysed by refluxing it in 1:1 conc. HCl (60 ml) for 4 h. Reaction mass is cooled to room temperature and pH is adjusted to ~7 to precipitate the free α-amino acid (9 g, 95%).

Step V:

In a typical procedure, a mixture of α-amino acid (47.3 mmol), pyridine (25 ml) and acid anhydride (0.284 mol) is refluxed for 5 h. Pyridine and excess acid anhydride are distilled off under reduced pressure. The residue is purified by column chromatography over silica to get pure a-amidoketone (81%).

Step VI:

In a typical procedure, the a-amidoketone (38.4 mmol) is refluxed with 15% conc HCl (100 ml) for 4 h. The reaction mixture is concentrated to dryness and titurated with 25 ml ethyl acetate to get α-ketoamine hydrochloride as a white crystalline solid (82%).

Step VII:

There are two different procedures which are followed for the conversion of the α-ketoamine hydrochloride to 4-hydroxy isothiazole. Procedure 1 is followed for α-acetoamine hydrochloride (Bull. Chem. Soc. jpn. 41, 1968, 959–964) and procedure 2 is employed for higher homologous a-ketoamine hydrochlorides.

Procedure 1:

To anhydrous DMF (10 ml/1 g of α-ketoamine hydrochloride), maintained at 0° C., is added dropwise thionyl chloride (12.5 mmol, 2.5 equivalents). After a lapse of 15 min, to this stirred solution is added α-ketoamine hydrochloride (5 mmol, 1 equivalent) at once. The reaction mixture is stirred at the same temperature for 2 h and then at room temperature for 2 h. The mixture is then poured on ice cold water (50 ml) and extracted with ether (3×50 ml). The organic layer is washed with water, dried over anhydrous $Na_2SO_4$ and concentrated under reduced pressure. The dark gummy residue is purified by column chromatography over silica gel to get 4-hydroxy isothiazole monomer and dimer in 12–28% yield.

Procedure 2:

Thionyl chloride (7 equivalents) is added dropwise to chloroform (20 ml/1 g of α-ketoamine hydrochloride) and maintained at 5° C. After a lapse of 15 min α-ketoamine hydrochloride (5 mmol, 1 equivalent) is added at once to the stirred solution. The reaction mixture is stirred at the same temperature for 2 h, then refluxed for 2 h. The mixture is then poured on ice cold water (100 ml) and extracted with dichloromethane (3×50 ml). The organic layer is washed with water, dried over anhydrous $Na_2SO_4$ and concentrated under reduced pressure. The residue is purified by column chromatography over silica gel to get 4-hydroxy isothiazole monomer in 48–63% yield.

5-arylcarbonyl-4-hydroxyisothiazoles are obtainable by the following reaction route:

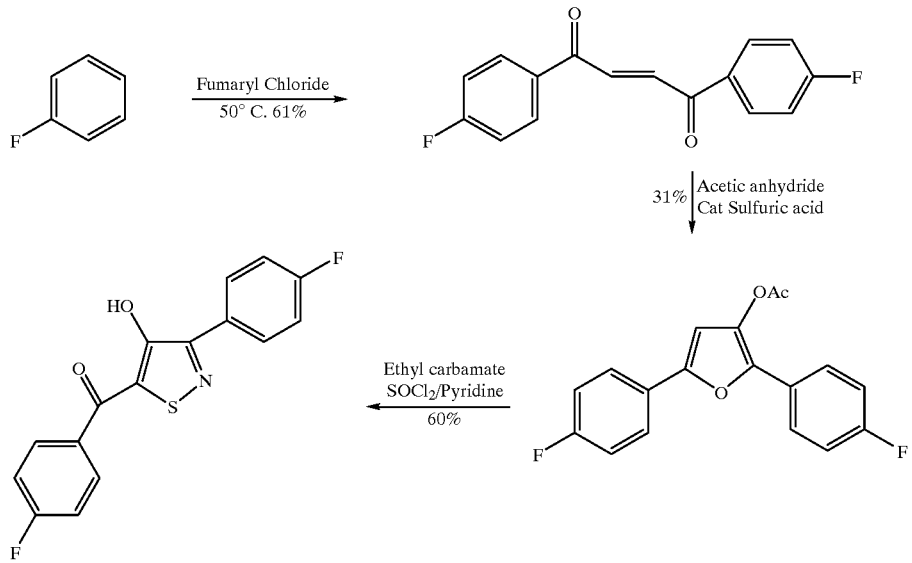

Pyridine (87 mmol, 31 equivalents) is added to a mixture of ethyl carbamate (22 mmol, 8 equivalents), thionyl chloride (22 mmol, 8 equivalents) in 30 ml of xylene. The mixture is stirred at room temperature for 30 min. Furan derivative (2.8 mmol, 1 equivalent) is added and the mixture is refluxed for 5 h. It is then poured in ice cold water (200 ml) and extracted with ethyl acetate (2×50 ml). The organic layer is washed with 2% $NaHCO_3$, water; dried over $Na_2SO_4$ and concentrated under reduced pressure. The residue is column chromatographed over silica gel to isolate 4-hydroxy isothiazole in 40–50%.

The 4-hydroxyisothiazole compounds according to the invention are thermally stable and antimicrobially effective compounds of low volatility and having a severely reduced tendency to migrate. They are therefore suitable for the antimicrobial finishing of polymeric compounds, for example in plastics, rubbers, paints, surface coatings, (textile) fibres which are exposed to a microbially contaminated environment.

Examples of polymers and other substrates which can be antimicrobially finished in this way are:

polymers of mono- and diolefins, polyolefins, copolymers of mono- and diolefins with one another or with other vinyl monomers, hydrocarbon resins, polystyrene, copolymers of styrene or α-methylstyrene or dienes or acrylic derivatives, graft copolymers of styrene or α-methylstyrene.

halogen-containing polymers, polymers derived from α,β-unsaturated acids and derivatives thereof, such as polyacrylates and polymethacrylates, polymers derived from unsaturated alcohols and amines or acyl derivatives or acetals thereof, homo- and copolymers of cyclic ethers, polyacetals, polyphenylene oxides and polyphenylene sulfides and mixtures thereof with styrene polymers or polyamides, polyurethanes derived from polyethers, polyesters and polybutadienes having terminal hydroxyl groups on the one hand and aliphatic or aromatic polyisocyanates on the other, and precursors thereof, polyamides and copolyamides derived from diamines and dicarboxylic acids and/or from aminocarboxylic acids or the corresponding lactams, polyureas, polyimides, polyamide-imides, polyetherimides, polyesterimides, polyhydantoins and polybenzimidazoles, polyesters, polycarbonates and polyester carbonates, polysulfones, polyether sulfones and polyether ketones, crosslinked polymers derived from aldehydes on the one hand and phenols, urea or melamine on the other hand, such as phenol-formaldehyde resins, urea-formaldehyde resins and melamine-formaldehyde resins, drying and non-drying alkyd resins, unsaturated polyester resins, crosslinkable acrylic resins, alkyd resins, polyester resins and acrylate resins, crosslinked epoxy resins, superabsorbent polymers natural polymers, such as cellulose, natural rubber, gelatine, and derivatives thereof modified chemically in a polymer-homologous manner, such as cellulose acetates, cellulose propionates cellulose butyrates, or the cellulose ethers, such as methylcellulose; and also rosins and derivatives.

The invention thus also provides a composition comprising (A) an organic material to be antimicrobially finished and (B) at least one compound of the formula (1) or formula (2).

The invention also relates to a process for the antimicrobial finishing of an organic material, which comprises adding at least one compound of the formula (1) or formula (2) thereto, and to the use of the compound of the formula (1) or formula (2) for the antimicrobial finishing of polymeric materials.

The amount of antimicrobial active substance to be used depends on the organic material to be antimicrobially finished and on the intended use of the material finished in this way. The composition according to the invention generally comprises, per 100 parts by weight of component (A), from 0.01 to 15 parts by weight, in particular from 0.05 to 10 parts by weight, and especially from 0.1 to 5 parts by weight of the antimicrobial active substance (component (B)).

The antimicrobial active substance (component (B)) can also be a mixture of two or more compounds of the formula (1) or formula (2). The compositions according to the invention can, in addition to the compounds according to the invention, also comprise other additives, for example antioxidants or light protection agents.

Incorporation into the organic polymers, for example into the synthetic organic, in particular thermoplastic, polymers can take place by adding the 4-hydroxyisothiazole compound according to the invention and, if desired, other additives by the methods customary in the art. Incorporation can expediently take place before or during shaping, for example by mixing the pulverulent components or by adding the antimicrobial active substance to the melt or solution of the polymer, or by applying the dissolved or dispersed compounds to the polymer, if desired with subsequent evaporation of the solvent. Another method of incorporating the mixtures according to the invention into polymers involves adding the former before or during polymerization of the corresponding monomers or before crosslinking.

The mixtures according to the invention can also be added to the organic polymers to be finished in the form of a masterbatch which comprises these compounds, for example, in a concentration of from 2.5 to 25% by weight.

The resulting antimicrobially finished polymer compositions can be converted into shaped articles, for example fibres, films, tapes, sheets, multi-wall sheets, containers, tubes and other profiles, by conventional methods, for example by hot pressing, spinning, extrusion or injection moulding.

The 4-hydroxyisothiazole compounds of the formula (1) or formula (2) are also suitable for the antimicrobial finishing of undyed and dyed or printed fibre materials made, for example, of silk, wool, polyamide, polyester or polyurethane, and in particular of cellulosic fibre materials of all types. Examples of such fibre materials are the natural cellulose fibres, such as cotton, linen, jute and hemp, and also pulp and regenerated cellulose. The 4-hydroxy-isothiazole compounds according to the invention are also suitable for the antimicrobial finishing of hydroxyl-group-containing fibres which are present in mixed fabrics, for example, of mixtures of cotton with polyester fibres or polyamide fibres. The 4-hydroxy-isothiazole compounds of the formula (1) or formula (2) are also suitable for incorporation into non-wovens.

"Non-woven" is a type of fabric that is not spun and woven into a cloth, but instead bonded together. According to the ISO definition it is a manufactured sheet, web, or batt of directionally or randomly orientated fibres, bonded by friction, and/or adhesion.

Nonwoven textiles are widely used in disposable as well as durable goods, such as baby diaper, feminine hygiene, adult incontinence, wipers, bed linings, automotive industries, medical face masks, air and water filtration, home furnishing and geotextiles. Such materials can be fabricated by different techniques, such as spunbonding, melt blown, carded thermal bonding and carded chemical bonding, dry and/or wet laid and needlefelts. Because of the nature of such applications, increasingly the market is demanding products with specific properties such as antimicrobial efficacy.

For this purpose, one or more compounds of the formula (1) or formula (2) are advantageously applied to the textile fibre material in an amount of from 0.01 to 20% by weight, preferably 0.1–3% by weight, and in particular from 0.25 to 2% by weight, based on the weight of the fibre material, in a process analogous to dyeing.

The 4-hydroxyisothiazole compounds according to the invention can be applied to the fibre material and fixed to the fibre in different ways, in particular in the form of aqueous dispersions or printing pastes.

The textile fibre materials finished using the compounds of the formula (1) or formula (2) according to the invention have an excellent and long-lasting antimicrobial protection.

An antimicrobial textile treatment formulation has, for example, the following composition:

20% by weight of a compound of formula (1) or formula (2),

5% by weight of sodium lauryl sulfate,

10 % by weight of an ethoxylated fatty alcohol,

40% by weight of propylene glycol and

25% by weight of water.

The 4-hydroxyisothiazole compounds according to the invention can also be used in paper finishing, printing thickeners containing starch, varnishes and paints.

The 4-hydroxyisothiazole compounds according to the invention are also useful for the disinfection and general antimicrobial treatment, such as deodorising, of the skin, mucous membrane and hair, preferably for the disinfection of hands and wounds.

Therefore, these compounds are suitable as an antimicrobial active substance in personal care products as shampoos, bath- and shower additives, hair-care products, liquid and bar soaps, lotions and cremes, deodorants, other aqueous or alcoholic solutions, for example cleaning solutions for the skin, moist cleaning sheets, oils and powders.

A further subject of the present invention is therefore a personal care composition comprising at least one compound of the formula (1) or formula (2) and cosmetically tolerable carriers or auxiliaries.

The personal care composition according to the present invention comprises 0.01 to 15, preferably 0.5 to 10 % b.w. of the 4-hydroxyisothiazole compounds of formula (1) or formula (2) and cosmetically tolerable carriers or auxiliaries.

The personal care composition according to the invention can be formulated as a water-in-oil or oil-in-water emulsion, as an oil-in-alcohol lotion, as a vesicular dispersion of an ionic or non-ionic amphiphilic lipid, as a gel, solid stick, aerosol formulation or a surfactant based formulation, such as a soap or skin cleanser.

As a water-in-oil or oil-in-water emulsion, the cosmetically compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any conventionally usable emulsifier can be used for the cosmetic composition according to the invention, for example one or more ethoxylated esters of natural derivatives, e.g. polyethoxylated esters of hydrogenated castor oil; or a silicone oil emulsifier, e.g. a silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic composition may also comprise further components, e.g. emollients, emulsion stabilisers, skin humectants, skin tanning accelerators, thickeners, such as xanthan, moisture-retention agents, such as glycerol, preservatives, perfumes and colourings.

The preparation of the cosmetic composition can be effected by physically mixing the antimicrobial(s) with the auxiliary by customary methods, for example by simply stirring the individual components together.

Cosmetic formulations include a very wide range of cosmetic products. Suitable products are, for example, especially the following:

skin-care products, for example skin washing and cleansing products in the form of bars of soap or liquid soaps, syndets or washing pastes, skin emulsions, multiple emulsions or skin oils;

bath products, for example liquid (foam baths, milks, shower products) or solid bath products, such as bath pearls and bath salts;

decorative body-care products, for example face make-ups in the form of day or powder creams, face powders (lose and compressed), rouge or cream make-ups, eye-care products, for example eye shadow products, mascara, eyeliners, eye creams or eye-fix creams; lip-care products, for example lipstick, lip gloss, lip liner, nail-care products, such as nail varnish, nail varnish remover, nail hardeners or cuticle removers;

feminine hygiene products, such as feminine hygiene washing lotions or sprays;

foot-care products, for example foot baths, foot powders, food creams or foot balms, special deodorants and antiperspirants or products for scrubbing off callouses;

sunscreens, such as sun milks, lotions, creams, oils, sunblockers or tropicals, pre-sun products or after-sun products;

suntanning products, for example self-tanning creams;

depigmenting products, for example products for bleaching or lightening skin;

insect repellents, for example insect oils, lotions, sprays or sticks;

deodorants, for example deodorant sprays, non-aerosol sprays, deodorant gels, sticks or roll-ons;

antiperspirants, for example antiperspirant sticks, creams or roll-ons;

products for cleansing and treating impure skin, for example syndets (solid or liquid), peeling or scrubbing products or peeling masks;

chemical depilatory products, for example depilatory powders, liquid depilatory products, creamy or pasty depilatory products, depilatory gels or aerosol foams;

shaving products, for example shaving soap, foaming shaving creams, non-foaming shaving creams, shaving foams and gels, preshaving products for dry shaving, after-shaves or aftershave lotions;

scents, for example perfumes (Eau de Cologne, Eau de Toilette, Eau de Parfum, Parfum de Toilette, perfume), perfume oils or perfume creams;

products for oral and dental hygiene as well as for dentures, for example toothpastes, tooth gels, tooth powders, mouth-wash concentrates, anti-plaque mouth-washes, denture cleaning products or denture adhesion products;

cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening products, liquid hair fixatives, hair foams, hair sprays, bleaching agents, for example hydrogen peroxide solutions, bleaching shampoos, bleaching creams, bleaching powders, bleaching pastes or oils, temporary, semitemporary or permanent hair dyes, products containing self-oxidising dyes, or natural hair dyes, such as henna or camomile.

An antimicrobial soap has, for example, the following composition:
- 0.01 to 5% by weight of a compound of the formula (1) or formula (2),
- 0.3 to 1% by weight of titanium dioxide,
- 1 to 10 % by weight of stearic acid,
- to 100% of soap base, for example the sodium salts of tallow fatty and coconut fatty acid or glycerols.

A shampoo has, for example, the following composition:
- 0.01 to 5% by weight of a compound of the formula (1) or formula (2),
- 12.0% by weight of sodium laureth-2-sulfate,
- 4.0% by weight of cocamidopropylbetaine,
- 3.0% by weight of NaCl and water to 100%.

A deodorant has, for example, the following composition:
- 0.01 to 5% by weight of a compound of the formula (1) or formula (2),
- 60% by weight of ethanol,
- 0.3% by weight of perfume oil and water to 100%.

The personal care formulations listed above can be in a very wide range of forms of presentation, for example
- in the form of liquid formulations as an O/W emulsion,
- in the form of a gel,
- in the form of an oil, cream, milk or lotion,
- in the form of a powder, lacquer, pellets or make-up,
- in the form of a stick,
- in the form of a spray (spray with propellant or pumping spray).or an aerosol,
- in the form of a foam, or
- in the form of a paste.

The 4-hydroxyisothiazole compounds according to the invention are useful for the preservation of cosmetic and household products against microbial spoilage.

The oral hygiene composition may comprise an additional antibacterial enhancing agent, for example an anionic polymeric polycarboxylate, a dehydrated polyphosphate salt, a compound which provides a source of fluoride ions, a polishing material, including siliceous material or sodium bicarbonate, an orally acceptable vehicle, including a water-phase with humectant, thickeners, surface-active agents and a flavoring or sweetening material.

The oral hygiene composition according to the invention contains from 0.003 to 5% by weight based on the total weight of the composition, of antimicrobial or a mixture of antimicrobials of the formula (1) or formula (2).

The preparation of the oral hygiene composition can be effected by physically mixing the antimicrobial(s) with the other ingredients by customary methods, for example by simply stirring the individual components together, then mixing further under vacuum.

An oral care formulation has, for example, the following composition:
- 10 % by weight of sorbitol,
- 10 % by weight of glycerin,
- 15% by weight of ethanol,
- 15% by weight of propylene gylcol,
- 0.5% by weight of sodium lauryl sulfate,
- 0.25% by weight of sodium methyl cocyl taurate,
- 0.25% by weight of poloxypropylene/polyoxyethylene block copolymer,
- 0.10% by weight of mint flavor,
- 0.3% by weight of a compound of formula (1) or formula (2),
- 48.6% by weight of water.

The oral hygiene composition may be in various forms of presentation including the form of a gel, paste, cream or mouthwash.

Furthermore the 4-hydroxyisothiazole compounds according to the invention are useful as household cleaners for the cleaning and disinfection of hard surfaces.

A detergent has, for example, the following composition:
- 0.01 to 5% by weight of a compound of the formula (1) or formula (2)
- 3.0% by weight of octanol 4EO,
- 1.3% by weight fatty alcohol $C_8$–$C_{10}$-polyglucoside,
- 3.0% by weight isopropanol,
- water to 100%.

A better understanding of the present invention and of its many advantages will be had by referring to the following Examples, given by way of illustration.

EXAMPLE 1

Synthesis of Dibenzyl Ketone

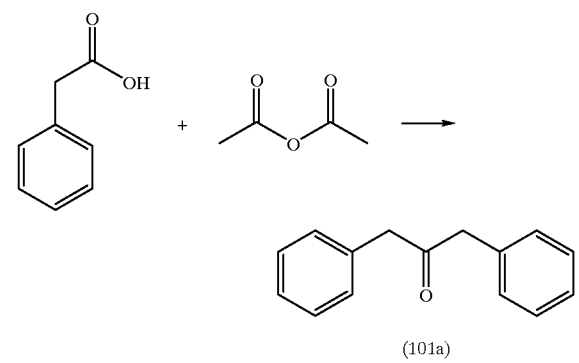

(101a)

In a 1 lit. three necked round bottom flask is added phenyl acetic acid (308 g) and acetic anhydride (285 g). Reaction mixture is refluxed at 150° C. for 3 h. Acetic anhydride is distilled off along with acetic acid formed and residue is kept overnight at room temperature. Residue is subjected to vacuum distillation at 5mm Hg pressure and bath temperature of 210° C.–225° C. Fraction distilled at 160° C.–200° C. is collected and treated with 5M NaOH solution (200 ml) and extracted with ethyl acetate (200 ml). The ethyl acetate is distilled off under reduced pressure to obtain dibenzyl ketone (136 g, 29% yield).

Synthesis of Oxime

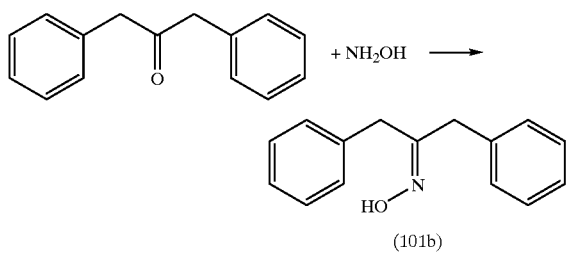

(101b)

In a 5 lit. sulfonation flask is added dibenzyl ketone (134 g), absolute ethanol (1 lit.), hydroxylamine hydrochloride (79.8 g), sodium hydroxide flakes (51.1 g) and water (60 ml). Reaction mixture is stirred for 1 h, then poured into cold water. Dilute hydrochloric acid is added and pH adjusted to 2. Solids precipitated are filtered and suck dried.

Wet weight=172.4 g Product is dried in oven at 60° C.
Dry weight=115.0 g (80% yield).

Synthesis of Tosylate

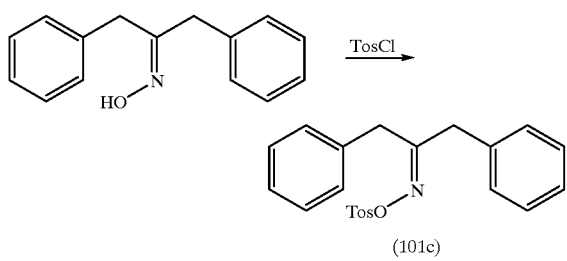

(101c)

In a 1 lit. three necked round bottom cooled in ice-bath are added oxime (123 g) and dry pyridine (490 ml) and stirred using mechanical stirrer. Tosyl chloride (107 g) is added in small lots to the stirred mixture maintaining temperature at 0° C. over a period of 1 h. Reaction mixture is stirred further at room temperature for 1.5 h. Reaction mixture is then poured in cold water and stirred. Solids precipitated are filtered and dried under vacuum for 6 h.

Dry weight (crude)=204 g.

Crude tosylate (119 g) is dissolved in ethyl acetate (600 ml), washed with brine. Ethyl acetate [75%] is distilled off and then further distillation is continued with addition of hexane until a large amount of solid seems to have separated. The separated solids are collected by filteration.

Weight=94.3 g (79% yield).

Synthesis of Aminoketone Hydrochloride

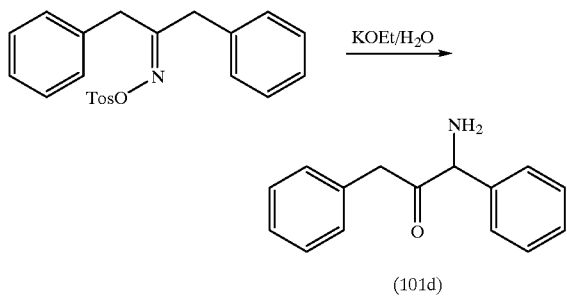

(101d)

In a 2 lit. three necked flask fitted with mechanical stirrer flushed with nitrogen is charged dry ethanol (400 ml) and cooled in ice-salt mixture to −13° C. Potassium metal (10.2 g) cut into small pieces is added over 1.5 h maintaining temperature of the solution below −2° C. The solution is stirred further for 0.5 h during which it cooled to −10° C. Tosylate (75 g) dissolved in dry THF (400 ml) was added to the solution over 1 h 15 min. maintaining temperature of the reaction mixture between −10° C. to −5° C. Reaction mixture was stirred further for 0.5 h at −5° C. Reaction mixture was then thawed to 20° C. over 2.5 h. It was then filtered and washed with ethanol (100 ml). Filtrate was cooled in ice-salt mixture under nitrogen and quenched with aqueous hydrochloric acid (conc. HCl 100 ml diluted with water to 300 ml) keeping temperature between 5° C.–10° C. Stirred further for 0.5 h maintaining temperature between 5° C.–10° C. Diluted with water (600 ml) and concentrated to a small volume approx. 300 ml] Again diluted with water (600 ml) and precipitated brown coloured solids were extracted with ethyl acetate (200 ml). Aqueous phase was concentrated under vacuum to about 200 ml. Diluted with ether (100 ml) and solids precipitated were filtered, washed with ether (100 ml) and dried under vacuum over $P_2O_5$ for 5 h.

Yield=21.9 g (42%).

Synthesis of 3,5-diphenyl-4-hydroxyisothiazole

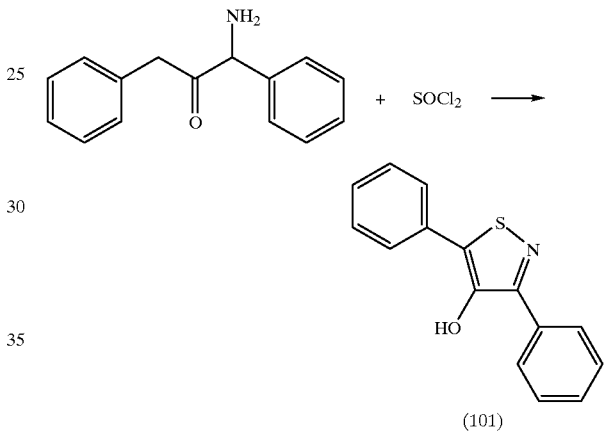

(101)

In a 250 ml three necked round bottom flask flushed with nitrogen is charged aminoketone hydrochloride (25.5 g). Dry DMF (110 ml) is added, stirred for 0.5 h. and cooled to −13° C. Thionyl chloride (27.3 ml) is added over 1.5 h maintaining temperature below 8° C. Reaction mixture is then thawed to 23° C. over 45 min. Reaction mixture is then heated on oil bath and maintained at 48° C.–53° C. for 1.5 h. Then heating is removed and stirred at room temperature for 15 h. Reaction mixture is poured into ice-water mixture (2.2 l) with stirring over 0.5 h. Solids formed are filtered and extracted in ether (700 ml). Ether layer is washed twice with water (200 ml each time) then extracted twice with 5% aqueous sodium hydroxide solution (300 ml each time). Aqueous phase is washed with ether (50 ml) and acidified with dilute hydrochloric acid (50 ml) while stirring. Solids precipitated are filtered and washed with water till neutral pH, then suck dried and dried under vacuum over $P_2O_5$ for 6 h.

Yield (crude)=19 g (77%).

Crude product is dissolved in ethanol (100 ml) and filtered. Filtrate is concentrated under vacuum to low volume and is stirred with hexane (80 ml) for 0.5 h. Solids filtered, washed with hexane (40 ml) and dried under vacuum over $P_2O_5$ for 2 h.

Yield=15.4 g (62%).

EXAMPLE 2

An agar incorporation test is carried out to determine the MIC (Minimum Inhibitory Concentration [ppm]) of the compound of formula (101):

| Medium: | Nutrient agar as test agar for bacteria: |
|---|---|
| | Mueller hinton agar to cultivate the aerobic bacteria |
| | Mueller hinton bouillon for obtaining the suspension of microorganisms |
| | Ethanol as solvent |
| | Wilkins-Chalgren agar to cultivate the anaerobic bacteria |
| | Sabouraud glucose agar to cultivate the dermatophytes |
| Examples of Test bacteria | *Staphylococcus aureus* ATCC 6538 |
| | *Corynebacterium xerosis* ATCC 373 |
| | *Staphylococcus hominis* DSM 20330 |
| | *Escherichia coli* NCTC 8196 |
| | *Aspergillus niger* ATCC 6275 |
| | *Candida albicans* ATCC 10231 |

Procedure

The test substances are dissolved in Ethanol, and a dilution series of the compound of the formula (2) in agar are prepared.

Anaerobic bacteria and dermatophytes are cultivated on agar-plates, and washes off with Mueller-Hinton bouillon. Aerobic bacteria are cultivated in Mueller-Hinton bouillon overnight. The test germ suspension are diluted with Mueller-Hinton bouillon to a density of McFarland standard 0.5.

10 µl of each germ suspension is dropped onto the agar plates containing the test substance, and the plates are then incubated at 36° C. for 2 to 3 days. (Aerobic bacteria are incubated at 36° C. for 48 hours, anaerobic bacteria are incubated at 30° C. for 72 hours). As controls, the bacterial suspensions are applied to agar plates without test substances. In order to exclude the solvent ethanol having an influence on the growth properties, the bacterial suspensions are applied to agar plates containing ethanol, but without test substance.

After the plates have been incubated, the growth of the bacteria on the test-substance-containing plates is compared with that of the control plates.

The minimum inhibitory concentration (MIC) is given as the lowest concentration which shows clear inhibition compared to the control.

The MIC values are given in the table 1 below.

TABLE 1

MIC (Minimum Inhibitory Concentration [(ppm)"] of the compound of formula (1)
Test Organisms

| *Staphylococcus aureus* ATCC 6538 | *Escherichia coli* NCTC 8196 | *Staphylococcus hominis* DSM 20330 | *Corynebacterium xerosis* ATCC 373 |
|---|---|---|---|
| 5 | 5 | 50 | 5 |

The results in the above table clearly show that the compounds have antimicrobial activity.

EXAMPLE 3

According to Example 2 the MIC of the compounds listed in the table below are tested:

| Compound | | SA | SH | EC | CA | AN |
|---|---|---|---|---|---|---|
| (102) | 3,5-diphenyl-4-hydroxyisothiazole | 10 | 50 | 5 | 50 | 13 |
| (103) | 3-phenyl-4-hydroxyisothiazole | 50 | 250 | 250 | 100 | |
| (104) | 3-benzyl-4-hydroxyisothiazole | 50 | 250 | 500 | 500 | |

-continued

| Compound | SA | SH | EC | CA | AN |
|---|---|---|---|---|---|
| (105) | 50 | | 50 | 50 | 10 |
| (106) | 500 | 500 | 500 | 500 | 100 |
| (107) | 5 | 5 | 0 | 0 | 0 |
| (108) | | 0 | 0 | 100 | 0 |
| (109) | 2 | 0 | 0 | 0 | |

Test Organisms
SA = *Staphylococcus aureus* ATCC 6538
SH = *Staphylococcus hominis* DSM 20328
EC = *Escherichia coli* NCTC 8196
CA = *Candida albicans* ATCC 10231
AN = *Aspergillus niger* ATCC 6275

What is claimed is:

1. An antimicrobial method, which comprises contacting a substrate with an antimicrobially effective amount of a compound of the formula

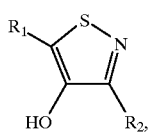

wherein $R_1$ and $R_2$ are independently of each other hydrogen; $C_1$–$C_{10}$ alkyl; substituted $C_1$–$C_{10}$ alkyl; $C_1$–$C_{10}$ acyl; substituted $C_1$–$C_{10}$ acyl; $C_6$–$C_{10}$ aryl; substituted $C_6$–$C_{10}$ aryl; $C_6$–$C_{10}$ arylcarbonyl; or substituted $C_6$–$C_{10}$ arylcarbonyl.

2. An antimicrobial method according to claim 1 wherein $R_1$ and $R_2$ are both $C_6$–$C_{10}$ aryl.

3. An antimicrobial method according to claim 1, which is carried out during finishing of, undyed and dyed or printed fibre materials.

4. A method for the antimicrobial treatment of skin, mucous membrane or hair which comprises applying an antimicrobially effective amount of a compound of the formula (1) according to claim 1 thereto.

5. A method for incorporating into and for the antimicrobial finishing of polymeric materials which comprises contacting the polymeric materials with an antimicrobially effective amount of a compound of the formula (1) according to claim 1.

6. A method for the antimicrobial treatment of a hard surface which comprises applying to the hard surface an antimicrobially effective amount of a compound of the formula (1) according to claim 1.

7. A method for the antimicrobial treatment of teeth and gums, which comprises applying an antimicrobially effective amount of a compound of the formula (1) according to claim 1 thereto.

8. A method for the preservation of cosmetic and household products against microbial spoilage, which comprises incorporating into the cosmetic and household products an antimicrobially effective amount of a compound of the formula (1) according to claim 1.

9. A personal care composition comprising at least one compound of formula (1) according to claim 1 and cosmetically tolerable carriers or auxiliaries.

10. An oral care composition comprising at least one compound of formula (1) according to claim 1.

11. A detergent composition comprising at least one compound of formula (1) according to claim 1.

12. A composition comprising an organic material to be antimicrobially finished and at least one compound of the formula (1) according to claim 1.

13. A process for the antimicrobial finishing of an organic material, which comprises adding at least one compound of the formula (1) according to claim 1 thereto.

14. A process for the antimicrobial finishing of undyed and dyed or printed fibre materials, which comprises adding at least one compound of the formula (1) according to claim 1 thereto.

15. A process for the antimicrobial finishing of nonwoven textile materials, which comprises adding at least one compound of the formula (1) according to claim 1 thereto.

* * * * *